United States Patent [19]

Mayer

[11] Patent Number: 5,212,993
[45] Date of Patent: May 25, 1993

[54] GAS SAMPLING SYSTEM AND METHOD

[75] Inventor: William N. Mayer, White Bear Lake, Minn.

[73] Assignee: Modern Controls, Inc., Minneapolis, Minn.

[21] Appl. No.: 870,898

[22] Filed: Apr. 20, 1992

[51] Int. Cl.$^5$ .............................................. G01N 1/24
[52] U.S. Cl. ..................................... 73/864.21; 73/52
[58] Field of Search ............ 73/864.41, 863.81, 864.87, 73/864.21, 864.85, 864.34, 864.81, 864.74, 52

[56] References Cited

U.S. PATENT DOCUMENTS

| | | | |
|---|---|---|---|
| 3,668,834 | 6/1972 | Deans | 73/864.81 |
| 4,133,736 | 1/1979 | Nakagawa et al. | 73/864.74 |
| 4,464,940 | 8/1984 | Pospisil | 73/864.81 |
| 4,835,109 | 5/1989 | Trisciani et al. | 73/864.21 |
| 5,099,679 | 3/1992 | Huerlimann et al. | 73/52 |

*Primary Examiner*—Hezron E. Williams
*Assistant Examiner*—Nashmiya Ashraf
*Attorney, Agent, or Firm*—Palmatier, Sjoquist & Helget

[57] ABSTRACT

An apparatus and method for extracting and measuring a gas sample from a package. The apparatus includes a hollow needle for puncturing the package, a suction pump for withdrawing a gas sample, and an intermediate sensor and valve to receive and direct gas flow through the system. The method includes puncturing the package, activating the suction pump for a predetermined time, equalizing the pressure drop across the sensor, and measuring the gas oxygen content.

7 Claims, 1 Drawing Sheet

GAS SAMPLING SYSTEM AND METHOD

BACKGROUND OF THE INVENTION

The present invention relates to a gas sampling system, more particularly to a system for extracting small quantities of gas from a sealed package for sampling purposes.

In the packaging industry there is a need for ensuring that the quality of packaging materials is suitable for the safe storage of the packaged contents. In particular, in the food packaging industry it is important that packaging materials be selected from a group of available materials to best preserve the contents of the package over an extended shelf life. Virtually any packaging material has some degree of permeability to oxygen, and therefore virtually any packaging will eventually permit sufficient oxygen leakage into the package so as to contaminate or spoil the contents. However, there is a wide variation in the permeability of various packaging materials, and therefore it is possible to select materials which, while permeable, do have a sufficient non-permeability to oxygen so as to adequately serve as a food packaging material.

It is conventional practice in the packaging industry to back-flush packages with nitrogen ($N_2$) before sealing the package. A further problem which is frequently encountered in this industry is the problem of poor sealing; a poor seal will permit oxygen leakage or permeation into the package, and can result in contamination or spoilage of the product contained within the package.

One of the periodic tests which are conducted in food processing plants, and in other plants where package permeability is of concern, is a test to measure the permeability of the packaging material. This test may be conducted by testing a sample of the packaging material in a device such as the Mocon "OXTRAN" test instrument, where an actual measure of permeability can be obtained. Although permeability testing of the packaging materials provides an excellent measure of the rate at which oxygen will permeate through the materials, such a test cannot be performed to test the package seal. The package seal is best tested by extracting a sample of gas from the interior of the package and then conducting a test on the gas sample to measure the oxygen concentration in the gas sample. One of the prior art techniques for extracting a sample of gas from the interior of a package is to utilize a needle and syringe. The needle is used to puncture the package and the syringe withdraws a sample of the interior package gas for subsequent sampling. The gas sample is injected into suitable test instrumentation in order to measure the oxygen concentration of the gas. The method is prone to error because it is quite likely that the sample gas may become mixed with extraneous oxygen concentrations in the atmosphere and elsewhere during the several steps required for the testing process. Another form of testing has been utilized, consisting of puncturing a package with a hollow needle and pumping a quantity of the packaging gas into a test station for purposes of measuring oxygen concentration. Care must be taken in using this technique and other techniques to avoid pressure inequalities in the system, as pressure variations can cause erroneous readings of oxygen content. The present invention is related to this form of testing device, to provide an efficient and reliable system for obtaining the necessary gas sample.

SUMMARY OF THE INVENTION

The present invention utilizes a hollow needle for penetrating a package, the needle being coupled via a hose to a system for extracting gas from the package. The system comprises an oxygen sensor in flow communication with the hose, and a valving mechanism downstream from the oxygen sensor, the valving mechanism being coupled to an air pump. The air pump is initially activated via the valving to draw a continuous supply of ambient air, and the valve is switched at the time a test is to be conducted to couple the hose leading from the oxygen sensor directly into the air pump line, thereby drawing gas from the package into the oxygen sensor. After a predetermined time the valving is again switched to disconnect the air pump from the line and to leave a quantity of sample gas in the lines leading to and from the oxygen sensor, wherein the pressure drop across the oxygen sensor and package is zero.

It is the principal object of the present invention to provide a gas sampling system for extracting a precise quantity of gas from a package, and holding a sample in a pressure-equalized reservoir while measurement tests are made.

It is another object of the present invention to provide a gas sampling system which is economical and easy to operate.

It is a further object of the present invention to provide a gas sampling system which does not introduce contaminants into the sample.

The foregoing and other objects and advantages of the invention will become apparent from the following specification and claims, and with reference to the appended drawings.

DESCRIPTION OF THE PREFERRED EMBODIMENT

Figure 1:
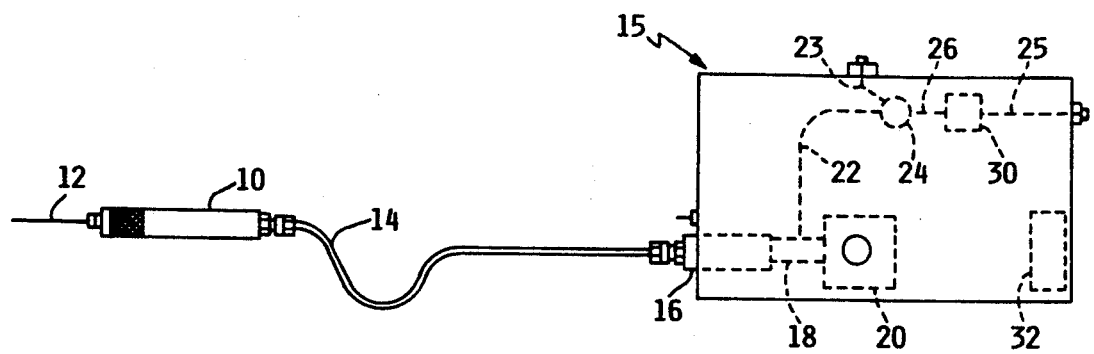
FIG. 1 shows a layout diagram of the present invention.

Referring first to FIG. 1, there is shown a schematic diagram of the invention. A hollow handle 10 has a hollow needle 12 embedded in one end and a gas tube 14 extending from the other end. Gas tube 14 is coupled into an analyzer housing 15, and more specifically into an inlet guide 16. Inlet guide 16 is coupled to a sensor assembly 18 which is connected to a heater 20. The sensor 18 is coupled via conduit 22 to a solenoid valve 24, and solenoid valve 24 is coupled via conduit 26 to an air pump 30. The electrical power for operating the air pump 30 and the solenoid valve 26 is obtained from a DC power supply 32 via wires (not shown). A second connection to solenoid valve 24 is made via conduit 23 which opens to the atmosphere.

Figure 2:
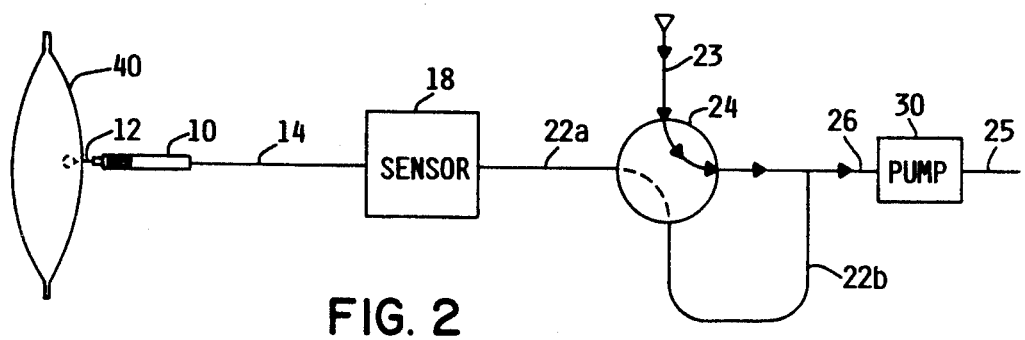
FIG. 2 shows a schematic block diagram of the present invention

FIG. 2 shows a schematic diagram of the invention in an operable mode. A package 40 is penetrated by needle 12 to insert the hollow point of needle 12 into the package 40. Solenoid valve 24 is initially positioned as illustrated in FIG. 2, wherein pump 30 is coupled to a conduit 23 which is opened to the atmosphere. Pump 30 therefore draws in air from the atmosphere and exhausts it via conduit 25 back into the atmosphere, under stabilized pumping conditions. Conduit 22a is closed, by virtue of the position of solenoid valve 24, which places a blocked termination over conduit 22a. When a test is to be conducted solenoid valve 24 is switched into its second position, the "test" position, thereby coupling conduit 22a to conduit 22b and thence to pump 30. In this position, pump 30 withdraws gas from within package 40 via the conduits herein described. Solenoid valve 24 is maintained in the "test" position for a brief period of time, and thereafter is switched back into position as shown in FIG. 2. At this switchover, conduit 22a again becomes blocked, but the gas passages from package 40 to the point of blockage of conduit 22a are now filled with a sample of the gas taken from the package 40. The sensor 18 may then be utilized to measure the oxygen content of the gas sample, which is converted into an electrical representation for display purposes.

Figure 3:
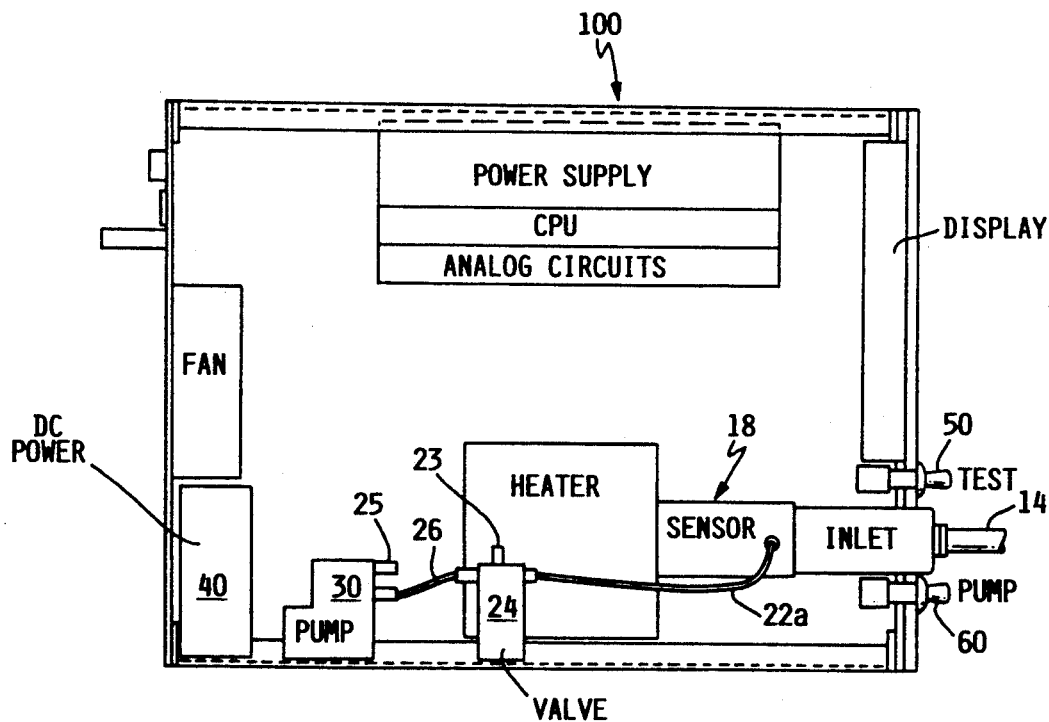
FIG. 3 shows a side view of an instrument containing the invention.

FIG. 3 shows an instrument 100 which contains the invention. The invention is best utilized by modification of an existing oxygen analyzer instrument for example, the Model HS-750 oxygen analyzer, manufactured by Ceramatec, Inc., of Salt Lake City, Utah, is readily adapted by addition of the other components of the invention described herein, to provide the necessary features and functions. The diagram of FIG. 3 shows many of the conventional components of the Ceramatec, Inc., Model HS-750, including a heater and sensor, power supply circuits, central processing units (CPU), analog circuits, display, and an internal fan all contained within a housing. Modification of these components may be made by converting the inlet of the Model HS-750 to accept a gas tube 14, mounting valve 24 and pump 30 inside the housing and adding a DC power supply 40 for providing the power necessary to drive the pump and valve. Valve 24 is preferably a Clippard valve, Model ETO-3-12 three-way valve, which is actuable by a 12-volt DC signal. Pump 30 is preferably a pump manufactured by Gilian Instrument Corp., West Caldwell, New Jersey, under Model Designation 801164. Pump 30 is a DC air pump which is operable by 12-volt DC power. Gas conduits 22a and 26 are interconnected between sensor 18 and valve 24, and between valve 24 and pump 30. Valve 24 has an exhaust outlet port 23, and pump 30 has an exhaust outlet port 25. For simplicity, none of the electrical interconnections are shown in FIG. 3.

The trace gas oxygen analyzer which forms a part of the HS-750 instrument comprises a zirconium sensor which is both temperature and pressure sensitive. The sensor must be calibrated, and is typically calibrated under ambient atmospheric pressure conditions. Because the accuracy of the sensor is sensitive to pressure variations it is important that the sensor readings under test conditions be also made under atmospheric pressure conditions. The instrument utilizes a heater in conjunction with the zirconium sensor to provide the necessary temperature control stability for reliable operation. After a gas sample has been placed in sensor 18 for a short period of time, the electronic circuitry of the Model HS-750 provides a visual numerical display of the oxygen content, and the system is also adapted for transmitting signals externally, which signals are representative of the measured oxygen content.

The test switch 50 which is added to the Model HS-750 functions to actuate the three-way valve 24; the normal position of the three-way valve provides a flow conduit from inlet port 23 to the pump 30, so that the operation of the pump will merely draw ambient air from within the instrument through the valve and pump. When test switch 50 is depressed, the three-way valve 24 provides a flow path between input conduit 22a and conduit 26, thereby permitting pump 30 to draw gas by suction from sensor 18. Switch 60, which has been added to Model HS-750, is merely a power switch to turn the pump on and off.

In the preferred embodiment, when a package is to be tested according to the principles of the invention, an adhesive rubber strip is first applied to the package to be tested. The hollow needle is then inserted into the package through this rubber strip, which minimizes leakage, so that the open end of the needle is well within the package. The "pump" switch 60 is turned on to permit the pump to begin operating, thereby drawing air through inlet 23 of valve 24. Next, the "test" switch 50 is depressed for a time period of approximately 5 seconds. This is the time period required to purge the needle and gas conduits leading to the sensor, and to extract the desired volume of test gas into the sensor; after this time period the "test" switch 50 is released. The operational electronics of the instrument will require approximately 2 seconds to provide an accurate reading of oxygen content, which is displayed on an LED display 70, located on the front panel of the instrument. During this time the needle is not removed from the package in order to preserve the desired pressure conditions.

The use of the invention preserves the necessary pressure equilibrium conditions in order to provide an accurate operation of the zirconium sensor. Prior to depressing the "test" switch 50, the pressure in sensor 18 is at equilibrium with the pressure inside and outside of the package to be tested. While the "test" switch 50 is being depressed, a vacuum is pulled on the sensor such that the sensor pressure is less than the interior package pressure, which is less than ambient pressure. After the "test" switch is released, the system returns to equilibrium, because the flexible package allows the two pressures to equalize to ambient pressure. Therefore, during the time in which the electronic circuitry in the instrument makes the necessary oxygen measurements the pressure within sensor 18 is at ambient pressure, which is the same pressure at which the sensor was calibrated.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. An apparatus for extracting and testing gas samples from sealed packages, comprising:
   a) a hollow needle adapted for puncturing said sealed package;
   b) a trace gas oxygen analyzer having an input and an output, and gas flow conduit means for passing gas from said hollow needle to said analyzer input;
   c) a valve having an output port and two selectable input ports, and gas flow conduit means for passing gas from said analyzer output to one of said valve input ports, the other of said valve input ports being open to ambient atmosphere;
   d) a gas pump connected to said valve output port; and e) means for actuating said valve for connecting said valve output port to either of said valve input ports.

2. The apparatus of claim 1, wherein said analyzer further comprises a zirconium sensor and means for heating said sensor to a predetermined temperature.

3. The apparatus of claim 1, wherein said valve further comprises a solenoid-operated valve, and said means for actuating said valve further comprises a switch.

4. The apparatus of claim 1, wherein said gas pump further comprises means for providing a suction at said valve output port.

5. The apparatus of claim 4, further comprising means for activating said pump for a predetermined time interval and then deactivating said pump.

6. The apparatus of claim 5, wherein said predetermined time interval further comprises approximately five seconds.

7. The apparatus of claim 4, further comprising means for equalizing the pressure in said sealed package and the pressure in said trace gas oxygen analyzer.

* * * * *